United States Patent [19]

Troup et al.

[11] Patent Number: 4,543,815
[45] Date of Patent: Oct. 1, 1985

[54] DEVICE FOR THE DETECTION OF FOREIGN COMPONENTS IN A GAS AND AN APPLICATION OF THE DEVICE

[75] Inventors: Alan Troup, Männedorf; Sigfrid Strässler, Baden-Dättwil; Hannes Güttinger, Stäfa; Gustav Pfister, Uetikon, all of Switzerland

[73] Assignee: Cerberus AG, Männedorf, Switzerland

[21] Appl. No.: 624,910

[22] Filed: Jun. 26, 1984

[30] Foreign Application Priority Data

Jul. 15, 1983 [CH] Switzerland ............... 3900/83
Oct. 3, 1983 [CH] Switzerland ............... 5367/83

[51] Int. Cl.[4] ............................................. G01N 15/00
[52] U.S. Cl. ........................................ 73/28; 340/628; 356/438
[58] Field of Search .................. 73/28; 340/628, 629, 340/630; 250/343, 564, 565; 356/438, 439, 440

[56] References Cited

U.S. PATENT DOCUMENTS

| | | | |
|---|---|---|---|
| 2,486,622 | 11/1949 | White, Jr. ............... | 250/343 |
| 2,966,092 | 12/1960 | Hartridge ............... | 356/438 |
| 3,312,826 | 4/1967 | Finkle ............... | 356/438 |
| 3,860,818 | 1/1975 | Stalded et al. ............... | 250/343 |
| 3,994,603 | 11/1976 | Paschedag ............... | 356/438 |

FOREIGN PATENT DOCUMENTS

| | | |
|---|---|---|
| 1038454 | 3/1959 | Fed. Rep. of Germany . |
| 1942942 | 3/1970 | Fed. Rep. of Germany . |
| 2742972 | 4/1979 | Fed. Rep. of Germany . |
| 3117757 | 11/1982 | Fed. Rep. of Germany . |
| 379974 | 7/1964 | Switzerland . |
| 561942 | 3/1975 | Switzerland . |

*Primary Examiner*—Stephen A. Kreitman
*Attorney, Agent, or Firm*—Werner W. Kleeman

[57] ABSTRACT

An aerosol detector, for instance a transmission measurement path in a measurement chamber, is provided for the detection of a foreign component in a gas, for instance of incendiary aerosols or smoke in air, and communicates with a reference chamber containing aerosol-free reference gas. The gas in the measurement chamber is periodically exchanged for uncontaminated gas from the reference chamber by a periodical volume alteration of the reference chamber so that, in the presence of aerosols, the aerosol concentration in the measurement chamber and the output signal of the aerosol detector are modulated. The modulation, i.e. the variable portion of the output signal, is an indication of the aerosol concentration or the smoke density. A particularly suitable application is smoke detection in air for the purpose of fire or incendiary reporting or for monitoring air pollution.

40 Claims, 7 Drawing Figures

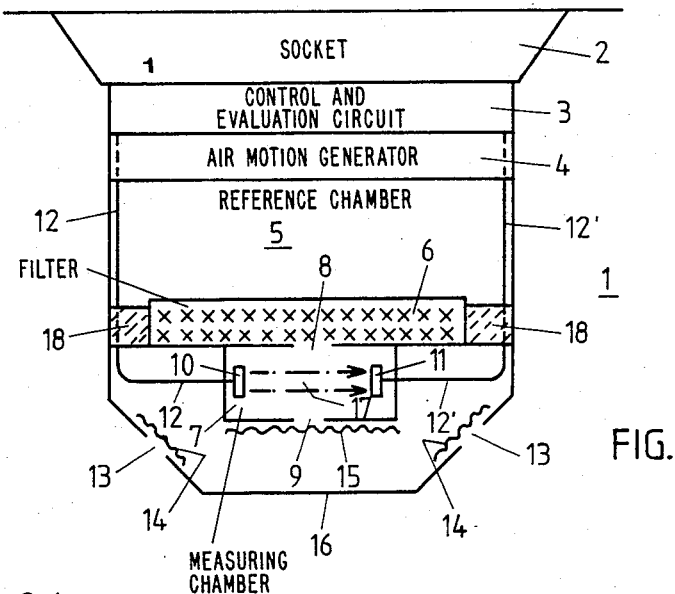
FIG. 1
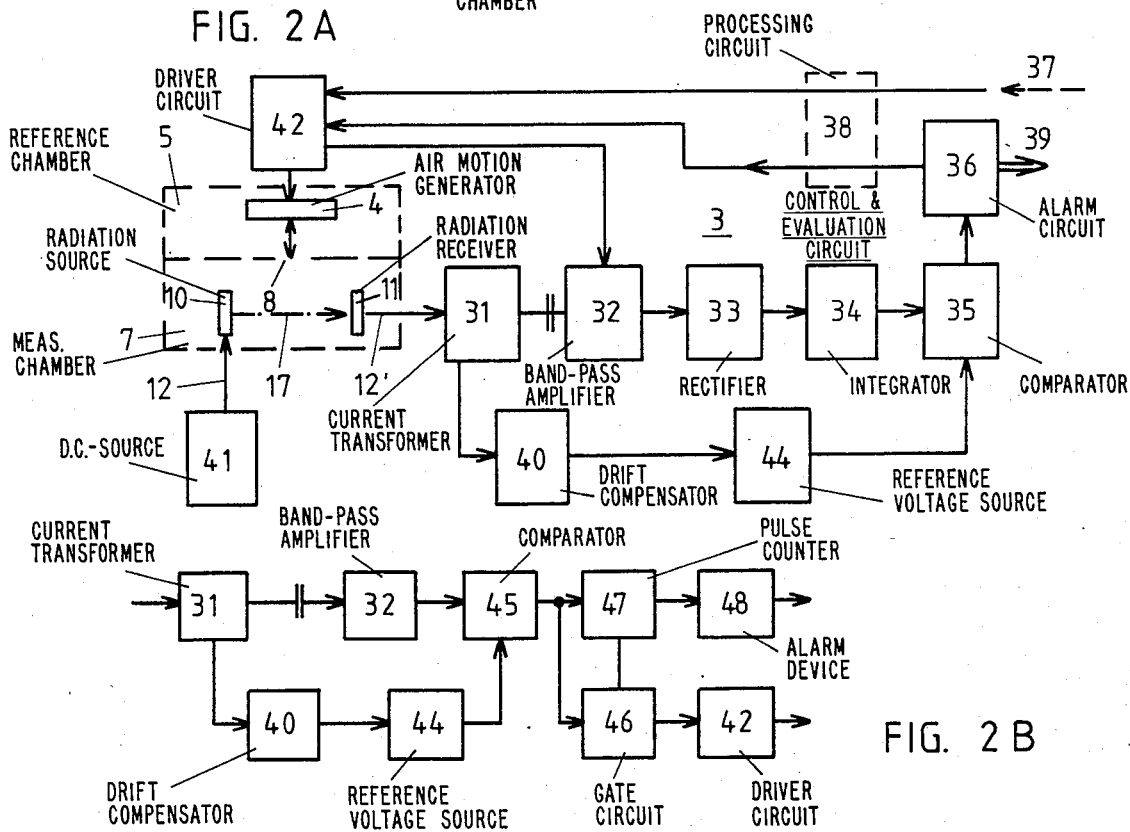
FIG. 2A
FIG. 2B

DEVICE FOR THE DETECTION OF FOREIGN COMPONENTS IN A GAS AND AN APPLICATION OF THE DEVICE

BACKGROUND OF THE INVENTION

The present invention broadly relates to gas detectors and, more specifically, pertains to a new and improved arrangement for detecting a foreign component contained in a gas and comprising a measurement chamber accessible to the gas to be investigated, a sensor generating an output signal in dependence of the foreign component content of the gas being investigated, and an electrical circuit for evaluating the output signal of the sensor. The invention also pertains to applications of the inventive arrangement.

Such an arrangement can, in principal, be employed for detecting any random solid, liquid or gaseous foreign components in a gas, in particular gas-born particles or aerosols. The sensor is then tuned or adapted to the foreign components and can, for instance, be constructed as a transmission measurement path exploiting the diminution or extinction of electromagnetic radiation. The employment of the arrangement for detecting incendiary aerosols or smoke particles in air, for instance for the purpose of incendiary or fire reporting, is of particular utility.

Hitherto, scattered radiation detectors in which the electromagnetic radiation scattered by smoke particles, i.e. visible light or infrared radiation, was registered by a scattered radiation receiver arranged outside the direct radiation path or beam were often employed for the detection of incendiary aerosols or smoke. Such a detector can be adjusted to be very sensitive, since in the absence of smoke there is no scattered radiation, i.e. the signal is nearly zero, and therefore in the presence of smoke only a small deviation from the zero value must be detected, which presents no great difficulties in measurement technology. It is, however, disadvantageous that such smoke detectors only react to radiation-scattering smoke, for instance to white smoke of high water vapor content, but react very little or not at all to black, preferentially radiation-absorptive smoke which scatters little or not at all.

In order to avoid this disadvantage and to simultaneously detect both radiation-scattering and radiation-absorbing smoke, it has proven advantageous to employ the transmission variability of a gas, for instance air, as a criterion for the presence of aerosols. The radiation extinction or diminution of a radiation beam transmitted by a source of radiation so as to traverse a transmission measurement path and picked up by a radiation receiver is evaluated to detect smoke. Since a relatively small deviation from a large standard value must be detected for this purpose, a relatively great length of the transmission measurement path is necessary for reliable detection of small smoke concentrations which, in practice, lies in the one meter range, a fact which considerably inhibits practical application and renders practical application nearly impossible without further measures.

In order to overcome this disadvantage and to avoid such large dimensions, it is known to employ a folded radiation beam or path in which the radiation is deflected by reflectors or mirrors so that, with a sufficient number of reflectors, the dimensions of the smoke detector can be reduced to a practically acceptable value in the ten centimeter (10 cm) range. In this case, however, the problem arises that radiation extinction or diminution of the type due to smoke can be counterfeited or mimicked by a reduction of reflectivity of the mirrors, for instance due to dust on the surfaces, as well as by aging of the source of radiation, and false alarms can be triggered. The smoke detector described in the German Patent Publication No. 3,117,757 attempts to avoid this disadvantage of gradual dust collection on the optics by employing a special stabilizing and regulating electronic circuit, so that gradual changes are compensated and a signal is only generated in response to rapid changes. However, a considerable amount of circuitry is required and furthermore a gradual development of smoke cannot be differentiated from a gradual collection of dust and can therefore not be recognized and detected.

Alternatively, smoke detectors have been variously proposed, e.g. in the German Pat. No. 1,038,454 and the Swiss Pat. No. 561,942 which comprise, in addition to the transmission measurement path itself, a reference measurement path having a different degree of radiation extinction or diminution or a different optical path length. Since, however, a very small difference between two large signals must be formed, a considerable amount of circuitry for electrical stabilization is required. Furthermore, precise mechanical adjustment and corresponding maintenance over long periods of time are required since such smoke detectors tend to mechanical instability and vibrational sensitivity.

In the smoke concentration measuring device described in the German Patent Publication No. 1,942,942 a reference beam path is renounced in order to avoid the disadvantages of a twin-beam method and, instead, the path length of the transmission measurement path is mechanically modulated, for instance by oscillating or vibrating a transparent termination window of the transmission measurement chamber or another component such as the radiation source, the radiation receiver or a reflector at a prescribed amplitude so that the optical path length varies between two values. The variable portion of the receiver output signal is an indication of the smoke density or concentration.

Such length modulation, however, only comprises a small portion of the total length of the transmission measurement path. In practice, for instance in incendiary or fire reporting applications, quite large modulation amplitudes lying at least in the centimeter range are necessary for achieving a sufficient smoke sensitivity. The reliability and the energy consumption of an oscillatory or vibratory generator system for such great amplitudes is, however, not compatible with the requirements of long term, maintenance-free and energy-saving operation for smoke detectors.

The smoke detection arrangement disclosed in the U.S. Pat. No. 2,486,622 takes a different direction in which the gas to be investigated is transported through a measurement chamber alternatingly directly and indirectly through a smoke-absorbing filter by means of a blower and a controllable valve. The variable portion of the output signal of the sensor constructed as a transmission measurement path or scattered light detector is an indication of the smoke concentration. It is, however, a disadvantage that the blower motor must be constantly in operation and must continuously deliver a considerable amount of air. Reliable, maintenance-free and energy-saving long term operation is therefore also not assured. In addition, the necessary filter can only absorb a certain quantity of aerosols, smoke or dust particles.

Low foreign particle concentrations always present in the air therefore cumulate rapidly on the filter and render the latter ineffective in a short period of time, so that in an alarm situation, for instance when a fire breaks out, the smoke generated is not detected unless the filter is exchanged, cleaned or regenerated at short time intervals.

SUMMARY OF THE INVENTION

Therefore, with the foregoing in mind, it is a primary object of the present invention to provide a new and improved construction of an arrangement for detecting a foreign component in a gas which does not exhibit the aforementioned drawbacks and shortcomings of the prior art constructions.

Another and more specific object of the present invention aims at providing a new and improved construction of a detection arrangement of the previously mentioned type which has smaller dimensions and in which precise, temporally stable and interference-insensitive detection, especially of smoke, is attainable without complicated, complex and unreliable optical and mechanical arrangements and electrical components and without requiring precise adjustment.

Yet a further significant object of the present invention aims at providing a new and improved construction of a detection arrangement of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the detection arrangement of the present invention is manifested by the features that a reference chamber is provided which is not directly accessible to the gas to be investigated and which contains a reference gas containing little or none of the foreign component to be detected. This reference chamber communicates with the measurement chamber by means of at least one aperture and comprises an air motion generator which periodically and alternatingly forces reference gas out of the reference chamber into the measurement chamber. The gas in the measurement chamber is at least partly displaced by the reference gas and the reference gas is again withdrawn into the reference chamber. The gas to be investigated enters into the measurement chamber. The electrical circuit evaluates the variable or alternating modulated portion of the output signal of the sensor as a criterion for the foreign component content.

In other words, the detection arrangement of the present invention is manifested by the features that it comprises a reference chamber not directly accessible to the gas being investigated, a reference gas contained in the reference chamber and having at least a lower foreign component content than the gas being investigated, at least one aperture for providing intercommunication between the reference chamber and the measurement chamber, the reference chamber comprising an air motion generator for periodically and alternatingly forcing the reference gas out of the reference chamber into the measurement chamber and withdrawing the reference gas back into the reference chamber, the reference gas at least partially replacing the gas in the measurement chamber when forced thereinto, the gas being investigated entering the measurement chamber when the reference gas is withdrawn, and the electrical circuit evaluating the alternating or variable component of the output signal of the sensor as a criterion for the foreign component content of the gas being investigated.

One application of the detection arrangement of the invention is characterized by the features that smoke particles generated by a combustion process are detected in air. Another application of the inventive arrangement is characterized by the feature that incendiary aerosols generated by a combustion process are detected in air.

It is particularly advantageous to construct the air motion generator such that it periodically alters the volume of the reference chamber and thereby periodically forces reference gas, e.g. uncontaminated air, out of the reference chamber into the measurement chamber and sucks it back again. It is advantageous to employ for this purpose a reference chamber wall which is constructed as an oscillating or vibrating membrane. With a relatively large oscillating or vibrating surface of the wall, a nearly complete or at least largely periodical gas exchange can be achieved in the measurement chamber even with modest oscillatory or vibratory amplitudes and low energy consumption. It is advantageous for the reference chamber volume to be equal to the measurement chamber volume and particularly advantageous for it to be greater.

The sensor can advantageously be constructed as an air-accessible transmission measurement path. A particularly good gas exchange can be obtained if the measurement chamber has a long or extended shape and comprises practically only the transmission measurement path, and wherein the openings or apertures to the reference chamber are constructed as slots extending substantially parallel to the transmission measurement path, thus achieving a particularly rapid air exchange.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various figures of the drawings there have been generally used the same reference characters to denote the same or analogous components and wherein:

FIG. 1 schematically shows a smoke detector in section;

FIGS. 2A and 2B diagramatically show evaluation circuits suited for the detector of FIG. 1;

DETAILED DESCRIPTION OF THE PREFERRED EMBODIMENTS

Figure 3:
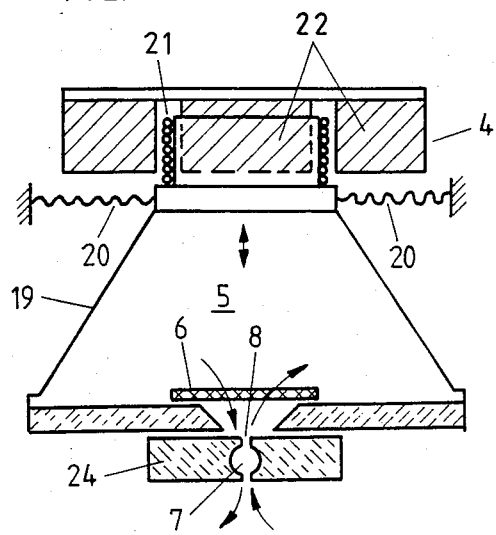
FIG. 3 shows an embodiment of a reference chamber.

Describing now the drawings, it is to be understood that to simplify the showing thereof only enough of the structure of the detection arrangement has been illustrated therein as is needed to enable one skilled in the art to readily understand the underlying principles and concepts of this invention. Turning now specifically to FIG. 1 of the drawings, the arrangement for aerosol detection and especially well suited for smoke detection and incendiary or fire reporting, which is illustrated therein by way of example and not limitation, will be seen to comprise a detector insert 1 which is insertable into a socket 2, e.g. a standard fire reporting or fire alarm socket. The detector insert 1 contains an electrical control and evaluation circuit 3, or at least a portion thereof, in which latter case the remainder of the circuit can be accommodated in a suitable signal center or central signal station connected with the socket 2 by conductors or lines and not particularly illustrated herein. An air motion generator 4 is controlled by the circuit 3 and forms a wall of the adjoining reference chamber 5 or a wall portion thereof and alters the volume thereof periodically at a prescribed frequency, preferably a frequency between 0.1 and 10 Hz, for instance 2 Hz. The air motion generator 4 can, for instance, be constructed as an electromagnetically, electrostatically, piezoelectrically or thermomechanically excitable or actuatable membrane in the manner of a loudspeaker or can comprise a piezo-foil of the type PVDF or contain a bimorphous piezoelectrical or bimetallic element. In a practically executed embodiment, a Philips woofer AD 4060/W4 proved to be well suited as an air motion generator. The reference chamber 5 serves as a reservoir for a reference gas which contains little or none of the aerosols to be detected, for instance clean, smoke-free air.

The reference chamber 5 communicates with the measurement chamber 7 proper, which is constructed as a transmission measurement chamber in the illustrated embodiment, through one or more communication openings or apertures 8 of small cross section in the range of 0.1 cm$^2$. The measurement chamber 7 comprises a volume of about 0.75 cm$^3$ which is smaller than that of the reference chamber's volume of about 100 cm$^3$, so that the ratio of the volumes is greater than 1:100. When the air motion generator, respectively the reference chamber wall 4, oscillates or vibrates, a volume of reference gas, i.e. uncontaminated or less smoke-laden air, corresponding to the oscillatory or vibratory amplitude is forced out of the reference chamber 5 through the apertures 8 into the measurement chamber 7, where it periodically displaces the air to be investigated.

An air-permeable but smoke-impermeable filter 6 which has a gas-specific surface upon which the smoke particles can accumulate and which may comprise, for instance, a fiber glass mat is provided in the reference chamber 5 ahead of the apertures 8 leading to the measurement chamber 7. The filter 6 prevents smoke aerosols from being entrained into the reference chamber 5 when the air is periodically reciprocated from the reference chamber 5 into the measurement chamber 7, so that uncontaminated air is always available as a reference gas. Furthermore, a smoke absorption medium 18 can be provided in the reference chamber 5, which may, for instance, contain activated carbon, glass fibers, filter cloth, filter paper, electrostatic filters or smoke-adsorbing surfaces and which absorbs any traces of smoke having nevertheless penetrated into the reference chamber 5. When the smoke absorption medium 18 is arranged in proximity to the apertures 8, the filter 6 can even be dispensed with and these apertures 8 remain open.

The measurement chamber 7 in the illustrated embodiment is constructed as a transmission measurement chamber and contains a source of radiation 10, for instance of the type Siemens SFH 400, which transmits electromagnetic radiation, such as visible light or infrared radiation, and a radiation receiver 11 which picks up direct radiation from the source of radiation 10 and may, for instance, be of the type Siemens BPY 64 P. The source of radiation 10 and the radiation receiver 11 are connected with the electrical circuit 3 by means of electrical conductors or lines 12 and 12'. The intermediate space 17 between the source of radiation 10 and the radiation receiver 11 forms the transmission measurement path with an effective length of only a few centimeters. It will be understood that the source of radiation 10 and the radiation receiver 11 can also be arranged outside of the measurement chamber 7 and the measurement chamber 7 can be irradiated through radiation-transparent windows. The measurement chamber 7 in the illustrated embodiment is surrounded by a housing 16 and communicates with the interior thereof through further apertures 9 which may be provided with a dust separator 15. The housing 16, in turn, comprises apertures 13 through which the ambient or external air can enter or penetrate into the interior by passing through further dust separators 14 or, respectively, a labyrinthine light trap and wind-retarding shielding.

In operation of the arrangement described, air is periodically reciprocated at a prescribed frequency, e.g. 2 Hz, between the reference chamber 5 and the measurement chamber 7 and thereby also between the measurement chamber 7 and the outside or external atmosphere or environment. The total volume of moved air should advantageously correspond to approximately the volume of the measurement chamber 7. In this manner the measurement chamber volume is at least partly, and in the ideal case as fully as possible, periodically exchanged, and external ambient air and uncontaminated air from the reference chamber 5 are alternatingly present in the measurement chamber 7 and therefore also in the transmission measurement path 17 between the source of radiation 10 and the radiation receiver 11. The moved volume depends upon the particular geometrical configuration of both chambers 5 and 7 and of the apertures 8 as well as upon the properties of the filter 6.

As long as no radiation-diminishing or radiation-attenuating smoke aerosols are present in the external ambient air, the intensity of the radiation received by the radiation receiver 11 remains unchanged and constant. However, as soon as the external ambient air contains smoke, the air in the measurement chamber 7 periodically alternates between smoke-free or smoke-poor air from the reference chamber 5 and smoke-laden air from the external atmosphere. Therefore, the intensity of the received radiation periodically varies with the frequency of the air exchange in the measurement chamber 7, i.e. an alternating or variable signal having the operating frequency of the air motion generator 4, i.e. a modulated signal, is conducted through the conductor 12' to the electrical evaluation circuit 3. When the source of radiation 10 is operated with the preferred direct-current, a DC-signal is superimposed upon the alternating or variable signal. When the source of radiation 10 is operated in the equally possible pulse mode of substantially different frequency, an alternating signal of different frequency is superimposed upon the alternating or variable signal. The alternating or variable signal modulated at the air motion frequency can be separated from the DC-component or from the alternating signal of different frequency in simple manner by the evaluation circuit 3 and is directly proportional to the smoke density.

In the procedure described, it is important that in the normal case, i.e. for smoke-free air, the evaluated signal be approximately zero and that a signal practically different from zero only then be generated when smoke is present in the external ambient air. The signal therefore does not arise from taking the difference of two signals and the requirements for stabilization are correspondingly much lower than in previously known procedures.

It is particularly advantageous that a sufficient air exchange in the measurement chamber 7 and in the transmission measurement path 17 can be attained with a very low oscillation or vibration amplitude of the air motion generator 4 in the micrometer range and with correspondingly low power consumption. The modulation amplitude of the radiation beam and of the output signal thereby achieved almost reaches the maximum possible value and is at least an order of magnitude greater than in previously known direct length modulations of the transmission measurement path 17. In a practically executed embodiment, it was found that a smoke density or concentration of 0.4%/meter can be detected reliably and free of interference with a simple uncomplicated evaluation circuit in the manner described using a transmission path length of less than 10 cm.

For the evaluation of the alternating or variable signal, i.e. the modulated signal, any suitable conventional alternating signal measuring or alarm circuit well known to one skilled in the art can in principal be employed. FIG. 2A shows a suitable embodiment as a block diagram in which the choice of the commercially available components is familiar to persons skilled in the art.

In this circuit, the source of radiation 10 is driven by a direct-current source 41 through the conductor 12 and transmits radiation through the transmission path 17 to the radiation receiver 11. The output signal of the radiation receiver 11 travels through the conductor 12' to a current transformer 31 and thence to a band-pass amplifier 32 which preferentially transmits only the frequency of the air motion generator 4, respectively of the driver 42 thereof. The output signal then passes via a rectifier 33 and an integrator 34 to a comparator 35 which compares the integrated signal with a reference signal and triggers an alarm circuit 36 as soon as the integrated signal exceeds a prescribed threshold value, i.e. when the smoke density or concentration remains above a prescribed value during a period of time determined by the time constant of the integrator 34. Additionally, the radiation receiver 11 can control a drift compensator 40 which regulates the reference voltage source 44 according to the DC-portion of the receiver output signal, so that changes in the radiation intensity of the source of radiation 10 due to aging, temperature fluctuations, dust accumulation or maladjustment can be automatically compensated. In an embodiment of the evaluation circuit as an alarm circuit, the level of the alarm threshold can be held constant in this manner. Such compensation can be of particular importance in an embodiment of the evaluation circuit as a measurement circuit if the exact value of the aerosol or smoke density or concentration is to be measured.

The alarm circuit 36 is constructed to generate an electrical signal in an alarm situation which has a frequency in the audible range and is conducted to the driver circuit 42 of the air motion generator 4. This induces the latter to irradiate an acoustical signal in the audible range in addition to the low frequency oscillations or vibrations below the audible range in order to call the attention of persons in the vicinity to the alarm state. This acoustic alarm signal is advantageously so designed that it attracts the greatest possible attention, for instance as a dissonance, as a tone of variable frequency or as a tone sequence. Alternatively, a speech signal can be broadcast which calls attention to the danger state in understandable language and supplies suitable behavior instructions. The alarm circuit 36 can comprise a suitable acoustic storage medium for this purpose.

Furthermore, an alarm state of the alarm circuit can be transmitted as a signal to a suitable central signal station or to an external alarm signal generator 39. The central signal station processes the signals arriving from the individual detectors and distributes them as required to the corresponding posts or locations, so that, for instance, suitable countermeasures may be taken. It can also be advantageous to receive the alarm signals of other, for instance neighboring, detectors 37, so that a detector not only signals the state of its own detection arrangement but also the state of neighboring detectors. It is advantageous for the acoustical signals triggered by the various detectors to be different from one another. If such signals are speech signals, suitable control means can make known in understandable language the location of the danger state, i.e. the location of the responding detector.

The signals of the individual alarm circuits 36, 37 can also be conducted to a processing circuit 38, which may be equipped with a microprocessor, and which, considering the states of all detectors, acoustically indicates the most practical behavior, for instance safe exit paths.

As in the modified embodiment of the circuit according to FIG. 2A that is shown in FIG. 2B, the alternating or variable output signal of the band-pass amplifier 32 can also be conducted directly to the input of a comparator 45 whose threshold is controlled by the drift compensator 40 and the reference voltage source 44. The series of pulses arising from an input signal sufficient to constantly trigger the comparator 45 and due to smoke density is conducted to the count input of a pulse counter 47. In the normal case, i.e. in the absence of a signal, the pulse counter 47 is continually reset by the driver circuit 42 through a gate circuit 46. When a signal occurs which is sufficiently large to trigger the comparator 45, the comparator output signal enables the gate circuit 46 for a time interval determined by a RC-time delay circuit. The pulse counter 47 therefore counts the signal pulses and triggers an alarm device 48 as soon as a prescribed count state is attained. The absence of pulses keeps the gate circuit 46 inhibited and the pulse counter 47 reset. The operation of this modified circuit is otherwise analogous to that of the previously described circuit according to FIG. 2A.

FIG. 3 shows a suitable embodiment for the construction of a reference chamber 5 with the associated air motion generator 4. A conically constructed wall 19 of the reference chamber 5 is fastened to a coil or armature 21 carried by a spring mounting 20 and extending into the core gap of a permanent magnet 22. When the coil 21 is excited by an alternating current, the membrane 19 oscillates or vibrates, as in an electrodynamic loudspeaker, and alters the volume of the reference chamber 5 periodically. This oscillation or vibration periodically forces the excess air out of the reference chamber 5 through the filter 6 and the aperture 8 into the measurement chamber 7 and sucks it back again.

Figure 4:
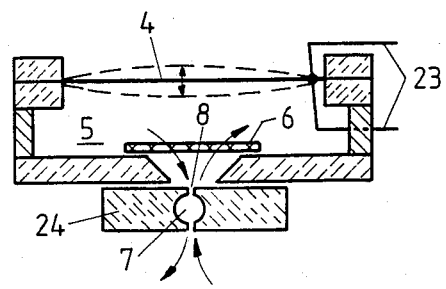
FIG. 4 shows a further embodiment of a reference chamber.

FIG. 4 shows a further embodiment of a reference chamber 5 in which the air motion generator 4 is constructed as a bimorphous piezo-foil. According to the voltage applied to each side of this piezo-foil by means of the conductors 23, the foil is correspondingly deflected. If an alternating current is applied to the conductors 23, then the piezo-foil oscillates or vibrates at a frequency corresponding to the applied alternating current and the reference chamber volume fluctuates at the same frequency.

Figure 5:
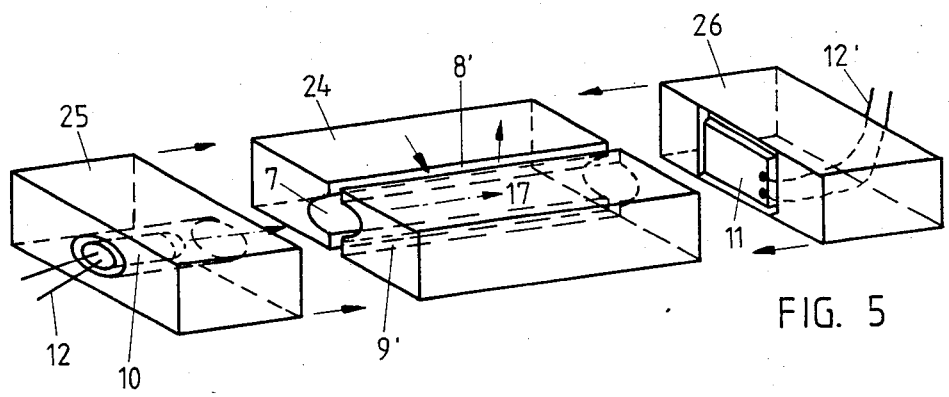
FIG. 5 shows an embodiment of a measurement chamber.

An advantageous embodiment of the measurement chamber 7 is illustrated in FIG. 5. The measurement chamber 7 in this embodiment comprises a lengthwise extending bore in a plastic body 24. Further plastic bodies 25 and 26 are attached at the long sides thereof and contain in central bores the source of radiation 10 and, respectively, the radiation receiver 11. A cross section of the bore 7 in the plastic body 24 advantageously corresponds to the form of the source of radiation 10. Instead of the cylindrical bore illustrated in the exemplary embodiment, another cross section can also be chosen, e.g. a square or rectangular cross section. In the embodiment described, the measurement chamber 7 comprises practically only the transmission measurement path 17 proper and no other dead volume.

Slot-shaped apertures 8' and 9' extending substantially parallel to the measurement chamber 7 or to the transmission measurement path 17 are provided on the flat sides of the plastic body 24. The measurement chamber 7 communicates with the reference chamber 5 on the one hand, as indicated in FIGS. 3 and 4, and with the housing interior and the external ambient atmosphere on the other hand, by means of such apertures 8' and 9'. It has been found that with this particular arrangement and configuration of the apertures a particularly effective and rapid air exchange between the measurement chamber 7 and the reference chamber 5 can be obtained, so that it suffices to select both volumes approximately equal. Even when the volume of the reference chamber 5 was chosen somewhat smaller than that of the measurement chamber 7, the air exchange was still intensive enough to detect even low smoke concentrations. In order to obtain the most optimum effect, it is also advantageous to adapt the temporal course of the volume alteration and of the air exchange to the given situation. For the geometrical arrangement described, it has for instance proven advantageous to choose a triangular time variation, while sinusoidal, rectangular or more complicated time courses or variations also produced good results.

Figure 6:
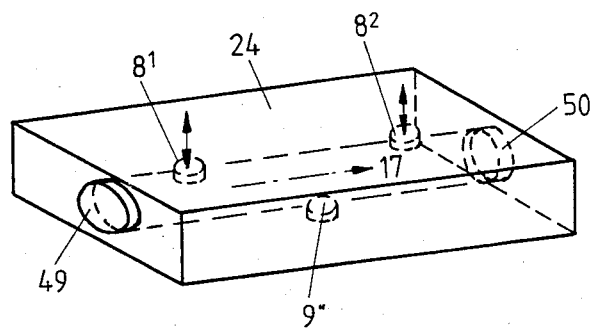
FIG. 6 shows a further embodiment of a measurement chamber.

As shown in FIG. 6, instead of connecting the measurement chamber and the reference chamber by a slot, a series of apertures can be provided in particularly advantageous manner between the chambers. The embodiment shows two apertures $8^1$ and $8^2$ on the reference wall side extending along the measurement path 17 and a central aperture 9" on the housing side. Two staggered rows of several apertures each can also be provided along the measurement path 17 instead.

While, as a rule, polychromatic radiation with a wide spectrum suffices for detecting smoke or for detecting solid or fluid particles suspended in a gas, the use of monochromatic radiation in the radiation absorption range of the foreign component to be detected is advantageous in detecting a given gaseous component in a carrier gas. In the embodiments according to FIGS. 1 or 5, this can for instance be achieved by constructing the source of radiation 10 as a monochromatic laser. In the embodiment according to FIG. 6, this can be achieved by providing a filter 49, respectively 50, with a suitable spectral transmission range on the radiation source side or on the receiver side or both.

It will be understood that the invention is not limited to the embodiments of smoke or aerosol detectors employing an optical measurement path as the aerosol sensor as heretofore described, but other aerosol detectors in which there is accomplished the task of determining a small deviation from a large standard value, e.g. an ionization chamber in which the ion current varies in dependence of the aerosol concentration, can be employed with analogous advantages.

It is also possible within the conceptual framework of the invention to construct the sensor as a smoke or gas sensitive quartz oscillator or as a capacitive sensor. It is also possible to construct the sensor as a scattered radiation sensor in which the unproblematical separation of the modulated radiation scattered by foreign particles from the uniform unmodulated or differently modulated interference radiation, for instance natural light or artificial light sources in the ambient environment, is of advantage.

Although the invention has proven to be particularly well suited for detecting smoke and aerosols, especially for the purpose of incendiary or fire reporting, it is not limited thereto. Other applications of the inventive arrangement are also possible, e.g. for detecting other air or gas-borne particles in a gas or in the air, for instance for monitoring combustion gases or air pollution. The invention can also be employed for detecting a foreign gas component in a gas if the sensor is tuned or adapted to the foreign gas to be detected and, for example, is constructed as a gas sensor reacting selectively to the foreign gas, for instance as an extinction or transmission path with monochromatic radiation in the absorption range of the foreign gas, instead of the polychromatic radiation usual in smoke detection.

The air motion generator as well as the electrical circuit can also be constructed in modified forms within the conceptual framework of the invention and can comprise practical and advantageous modified embodiments intended to improve operational reliability and resistance to interference. Long term operational reliability of a foreign component detector can thus be attained through the characteristic features of the invention without the necessity of a continuous suction or ingestion process afflicted with the previously mentioned disadvantages.

While there are shown and described present preferred embodiments of the invention, it is to be distinctly understood that the invention is not limited thereto, but may be otherwise variously embodied and practiced within the scope of the following claims. Accordingly,

What we claim is:

1. An arrangement for detecting a foreign component contained in a gas, comprising:
   a measurement chamber accessible to the gas being investigated;
   a sensor provided for the measurement chamber for transmitting an output signal in dependence of the content of the foreign component of the gas being investigated;

an electrical circuit for evaluating said output signal of said sensor;

a reference chamber not directly accessible to the gas being investigated;

a reference gas contained in said reference chamber and having a lower foreign component content than the gas being investigated;

means defining at least one aperture for providing intercommunication between the reference chamber and said measurement chamber;

the reference chamber comprising an air motion generator for periodically and alternatingly forcing said reference gas out of the reference chamber into the measurement chamber and for withdrawing the reference gas at least partially back into the reference chamber;

the reference gas at least partially displacing the gas being investigated in the measurement chamber when forced thereinto;

the gas being investigated entering the measurement chamber when the reference gas is withdrawn into the reference chamber; and said electrical circuit evaluating a modulated component of the output signal of the sensor as a criterion for the foreign component content of the gas being investigated.

2. The arrangement as defined in claim 1, wherein:
said lower foreign component content of the reference gas is zero.

3. The arrangement as defined in claim 2, wherein:
said air motion generator alters the volume of said reference chamber periodically at a prescribed frequency.

4. The arrangement as defined in claim 3, wherein:
said reference chamber comprises a wall portion; and
said wall portion being oscillatable such that oscillations thereof produce periodical volume changes of the reference chamber.

5. The arrangement as defined in claim 4, wherein:
said oscillatable wall portion of said reference chamber constitutes an electrodynamically excitable membrane.

6. The arrangement as defined in claim 4, wherein:
said oscillatable wall portion of said reference chamber constitutes an electrostatically excitable membrane.

7. The arrangement as defined in claim 4, wherein:
said oscillatable wall portion of said reference chamber constitutes a piezoelectrically excitable membrane.

8. The arrangement as defined in claim 4, wherein:
said oscillatable wall portion of said reference chamber constitutes a thermomechanically excitable membrane.

9. The arrangement as defined in claim 4, wherein:
said oscillatable wall portion is oscillatable at frequencies below the range of audible sound as well as at frequencies within the range of audible sound.

10. The arrangement as defined in claim 1, wherein:
the volume of said reference chamber is at least as great as the volume of said measurement chamber.

11. The arrangement as defined in claim 10, wherein:
the ratio of the volume of said reference chamber to the volume of said measurement chamber is at least 1:100.

12. The arrangement as defined in claim 1, wherein said sensor comprises:
a transmission measurement path;

a source of radiation for transmitting electromagnetic radiation;

said electromagnetic radiation traversing said transmission measurement path; and a radiation receiver for receiving the electromagnetic radiation having traversed the transmission measurement path.

13. The arrangement as defined in claim 12, wherein:
said source of radiation is capable of transmitting electromagnetic radiation in a spectral range in which the foreign component to be detected absorbs radiation.

14. The arrangement as defined in claim 13, wherein:
said source of radiation comprises a laser source for transmitting monochromatic radiation.

15. The arrangement as defined in claim 12, wherein;
said transmission measurement path comprises at least one filter having a spectral transmission range in the absorption range of the foreign component to be detected.

16. The arrangement as defined in claim 12, wherein:
said measurement chamber possesses substantially the form of said transmission measurement path.

17. The arrangement as defined in claim 16, wherein:
said transmission measurement path has a longitudinal direction of extent; and
said at least one aperture for providing communication between said measurement chamber and said reference chamber comprising a slot extending substantially in said longitudinal direction of the transmission measurement path.

18. The arrangement as defined in claim 17, wherein:
said measurement chamber comprises a further slot-shaped aperture for communicating with the ambient atmosphere and extending substantially in said longitudinal direction of said transmission measurement path.

19. The arrangement as defined in claim 16, wherein:
said measurement chamber and said reference chamber are mutually interconnected by a series of hole-shaped apertures arranged in said longitudinal direction of said transmission measurement path.

20. The arrangement as defined in claim 1, further including:
a filter provided between said measurement chamber and said reference chamber;
said filter being impermeable to the foreign component to be detected; and
the filter being permeable to said reference gas.

21. The arrangement as defined in claim 1, wherein:
said reference chamber comprises an absorption means for absorbing the foreign component to be detected.

22. The arrangement as defined in claim 1, wherein:
said electrical evaluation circuit comprises a frequency selective circuit having a transmission range.

23. The arrangement as defined in claim 22, wherein:
said air motion generator periodically alters the volume of said reference chamber at a prescribed frequency; and
said transmission range of said evaluation circuit lies at said frequency of periodic volume alteration of the reference chamber.

24. The arrangement as defined in claim 23, wherein:
said electrical evaluation circuit comprises a driver circuit; and said driver circuit both controlling said air motion generator and influencing said transmission range of said frequency selective circuit.

25. The arrangement as defined in claim 22, wherein:
said frequency selective circuit generates an output signal;
said output signal of the frequency selective circuit being integrated with a prescribed time constant;
said electrical evaluation circuit comprising a comparator; and
said comparator generating an output signal when said time-integrated output signal exceeds a prescribed threshold value.

26. The arrangement as defined in claim 22, wherein:
said frequency selective circuit generates an alarm signal;
said alarm signal of the frequency selective circuit being integrated with a prescribed time constant;
said electrical evaluation circuit comprising a comparator; and
said comparator generating an output signal when said time-integrated alarm signal exceeds a prescribed threshold value.

27. The arrangement as defined in claim 25, wherein:
said sensor generates a direct-current signal;
said electrical evaluation circuit comprising a compensation circuit for regulating said threshold value according to said direct-current signal; and
said output signal of the sensor controlling said compensation circuit.

28. The arrangement as defined in claim 22, wherein:
said frequency selective circuit generates an output signal;
said electrical evaluation circuit comprising:
a comparator for generating a series of pulses when said output signal of the frequency selective circuit exceeds a prescribed threshold value; and
a pulse counter for counting said pulses generated by said comparator and for triggering an alarm device when a prescribed count value is reached.

29. The arrangement as defined in claim 25, further including:
a driver circuit; and
said electrical evaluation circuit comprising an alarm circuit for both activating an alarm signal generator upon receiving said output signal from said comparator and controlling said air motion generator via said driver circuit for generating a signal in the audible range.

30. The arrangement as defined in claim 29, wherein:
said signal generated by said air motion generator when activated by said alarm signal generator comprises a speech signal.

31. The arrangement as defined in claim 29, wherein:
said air motion generator is controllable by alarm circuits of other detection arrangements in addition to the therewith associated alarm circuit.

32. The arrangement as defined in claim 29, wherein:
said driver circuit of said air motion generator is controllable by alarm circuits of other detection arrangements in addition to the therewith associated alarm circuit.

33. The arrangement as defined in claim 31, wherein:
said control signals of said alarm circuits all differ from one another in a manner characteristic of a particular detection arrangement.

34. The arrangement as defined in claim 31, further including:
a processing circuit for processing control signals of individual ones of said alarm circuits to acoustical behavior instructions; and
said acoustical behavior instructions being conducted to said air motion generator.

35. The arrangement as defined in claim 32, further including:
a processing circuit for processing control signals of individual ones of said alarm circuits to acoustical behavior instructions; and
said acoustical behavior instructions being conducted to said driver circuit of said air motion generator.

36. The arrangement as defined in claim 1, wherein:
said arrangement is used for detecting smoke particles generated by a combustion process in air.

37. The arrangement as defined in claim 36, wherein:
an incendiary alarm signal is triggered when smoke concentration exceeds a prescribed threshold value.

38. The arrangement as defined in claim 1, wherein:
said arrangement is used for detecting incendiary aerosols generated by a combustion process in air.

39. The arrangement as defined in claim 38, wherein:
an incendiary alarm signal is triggered when aerosol concentration exceeds a prescribed threshold value.

40. The arrangement as defined in claim 1, wherein:
said arrangement is used for detecting air pollution.

* * * * *